United States Patent
Roshanali et al.

(10) Patent No.: US 11,160,544 B2
(45) Date of Patent: Nov. 2, 2021

(54) DEVICE AND PROCEDURE FOR PERICARDIAL PATCH TRANSCATHETER ATRIAL SEPTAL DEFECT CLOSURE

(71) Applicants: Farideh Roshanali, Tehran (IR); Seyed Nasser Pourmoosavi, Tehran (IR); Ali Namazi, Tehran (IR)

(72) Inventors: Farideh Roshanali, Tehran (IR); Seyed Nasser Pourmoosavi, Tehran (IR); Ali Namazi, Tehran (IR)

( * ) Notice: Subject to any disclaimer, the term of this patent is extended or adjusted under 35 U.S.C. 154(b) by 435 days.

(21) Appl. No.: 16/288,534

(22) Filed: Feb. 28, 2019

(65) Prior Publication Data

US 2019/0192126 A1 Jun. 27, 2019

Related U.S. Application Data

(60) Continuation of application No. 15/338,419, filed on Oct. 30, 2016, now Pat. No. 10,219,796, which is a
(Continued)

(51) Int. Cl.
*A61B 17/00* (2006.01)
*A61B 17/04* (2006.01)
(Continued)

(52) U.S. Cl.
CPC ...... *A61B 17/0057* (2013.01); *A61B 17/0469* (2013.01); *A61B 17/0482* (2013.01);
(Continued)

(58) Field of Classification Search
CPC .............. A61B 17/0469; A61B 17/068; A61B 17/0482; A61B 17/0057; A61B 17/0643; A61B 2017/00615; A61B 2017/00575; A61B 17/12122; A61B 2017/0647; A61B 2034/2063; A61B 2017/00243; A61B 2017/00597; A61B 2017/1205;
(Continued)

(56) References Cited

U.S. PATENT DOCUMENTS

| 1,822,330 A | 9/1931 | Ainslie |
| 3,874,388 A * | 4/1975 | King ................... A61B 17/0057 606/232 |

(Continued)

OTHER PUBLICATIONS

Notice of Allowance dated Nov. 26, 2012 in U.S. Appl. No. 12/654,978.
(Continued)

*Primary Examiner* — Phong Son H Dang
(74) *Attorney, Agent, or Firm* — Farhad Shir

(57) ABSTRACT

A device for closure of an atrial septal defect (ASD) by deploying a pericardial patch includes a head including a distal jaw and a proximal jaw, and a distal disc attached to the distal jaw and a proximal disc attached to the proximal jaw. Each of the distal jaw and the proximal jaw includes at least one arm which closes when the distal disc moves forward and the proximal disc moves backward. Based on an engagement status of a distal engagement portion located on the at least one arm of the distal jaw with a proximal engagement portion located on the at least one arm of the proximal jaw, the pericardial patch deploys to close the ASD.

15 Claims, 10 Drawing Sheets

Related U.S. Application Data continuation-in-part of application No. 14/947,598, filed on Nov. 20, 2015, now Pat. No. 9,480,469, which is a continuation of application No. 13/835,587, filed on Mar. 15, 2013, now Pat. No. 9,192,365, which is a division of application No. 12/654,978, filed on Jan. 12, 2010, now Pat. No. 8,398,658.

(60) Provisional application No. 61/154,388, filed on Feb. 21, 2009.

(51) Int. Cl.
  *A61B 17/064* (2006.01)
  *A61B 17/068* (2006.01)
  *A61B 34/20* (2016.01)
  *A61B 17/12* (2006.01)

(52) U.S. Cl.
  CPC ........ *A61B 17/068* (2013.01); *A61B 17/0643* (2013.01); *A61B 17/12109* (2013.01); *A61B 17/12122* (2013.01); *A61B 17/12131* (2013.01); *A61B 2017/00243* (2013.01); *A61B 2017/00575* (2013.01); *A61B 2017/00597* (2013.01); *A61B 2017/00615* (2013.01); *A61B 2017/00946* (2013.01); *A61B 2017/0647* (2013.01); *A61B 2017/1205* (2013.01); *A61B 2034/2063* (2016.02)

(58) Field of Classification Search
  CPC .... A61B 17/12131; A61B 2017/00946; A61B 17/12109
  See application file for complete search history.

(56) References Cited

U.S. PATENT DOCUMENTS

| | | | |
|---|---|---|---|
| 4,007,743 A * | 2/1977 | Blake | A61B 17/0057 606/232 |
| 4,523,592 A | 6/1985 | Daniel | |
| 4,605,002 A | 8/1986 | Rebuffat | |
| 5,152,769 A | 9/1992 | Baber | |
| 5,250,058 A | 10/1993 | Miller et al. | |
| 5,356,424 A | 10/1994 | Buzerzk et al. | |
| 5,364,408 A | 11/1994 | Gordon | |
| 5,374,275 A | 12/1994 | Bradley | |
| 5,382,258 A | 1/1995 | Chow | |
| 5,387,221 A | 2/1995 | Bisgaard | |
| 5,843,098 A | 12/1998 | Allen et al. | |
| 5,853,422 A | 12/1998 | Huebsch | |
| 5,891,159 A | 4/1999 | Sherman et al. | |
| 6,048,351 A | 4/2000 | Gordon et al. | |
| 6,071,289 A | 6/2000 | Stefanchik et al. | |
| 6,290,674 B1 | 9/2001 | Roue et al. | |
| 6,464,707 B1 | 10/2002 | Bjerken | |
| 6,503,259 B2 | 1/2003 | Huxel et al. | |
| 6,565,581 B1 * | 5/2003 | Spence | A61B 17/11 606/153 |
| 7,018,387 B2 * | 3/2006 | Suyker | A61B 17/0644 606/153 |
| 7,666,198 B2 * | 2/2010 | Suyker | A61B 17/11 606/153 |
| 7,678,123 B2 * | 3/2010 | Chanduszko | A61B 17/0057 606/151 |
| 8,246,671 B2 | 8/2012 | Khairkhahan | |
| 9,295,456 B2 | 3/2016 | Subramanian | |
| 9,545,258 B2 | 1/2017 | Smith | |
| 10,441,259 B2 * | 10/2019 | Bippart | A61B 17/0057 |
| 2001/0047180 A1 | 11/2001 | Grudem | |
| 2002/0026159 A1 | 2/2002 | Zhu | |
| 2002/0100485 A1 | 8/2002 | Stevens et al. | |
| 2002/0169466 A1 * | 11/2002 | Peterson | A61F 2/064 606/153 |
| 2002/0183769 A1 * | 12/2002 | Swanson | A61B 17/115 606/153 |
| 2002/0183787 A1 * | 12/2002 | Wahr | A61B 18/1492 606/213 |
| 2003/0083674 A1 | 5/2003 | Gibbens, III | |
| 2003/0191482 A1 | 10/2003 | Suyker | |
| 2004/0143293 A1 * | 7/2004 | Marino | A61B 17/0057 606/213 |
| 2004/0181244 A1 | 9/2004 | Lee | |
| 2004/0186486 A1 | 9/2004 | Roue et al. | |
| 2004/0186489 A1 | 9/2004 | Lee | |
| 2005/0015101 A1 | 1/2005 | Gibbens et al. | |
| 2005/0043747 A1 | 2/2005 | Field et al. | |
| 2005/0065548 A1 * | 3/2005 | Marino | A61B 17/0057 606/213 |
| 2005/0080437 A1 | 4/2005 | Wright | |
| 2005/0216038 A1 | 9/2005 | Meade et al. | |
| 2005/0256532 A1 * | 11/2005 | Nayak | A61B 17/0057 606/151 |
| 2005/0273135 A1 | 12/2005 | Chanduszko | |
| 2005/0288786 A1 | 12/2005 | Chanduszko | |
| 2006/0069397 A1 | 3/2006 | Nobles | |
| 2006/0095052 A1 | 5/2006 | Chambers | |
| 2006/0190016 A1 | 8/2006 | Onuki et al. | |
| 2006/0282096 A1 | 12/2006 | Papa et al. | |
| 2008/0086075 A1 | 4/2008 | Isik | |
| 2009/0076541 A1 * | 3/2009 | Chin | A61B 17/0057 606/215 |
| 2009/0138029 A1 | 5/2009 | Saliman et al. | |
| 2010/0249491 A1 * | 9/2010 | Farnan | A61M 1/3653 600/16 |
| 2011/0066180 A1 | 3/2011 | Zeng | |
| 2013/0204275 A1 | 8/2013 | Agarwal | |
| 2015/0313598 A1 | 11/2015 | Todd | |
| 2016/0022252 A1 * | 1/2016 | Zhang | A61B 17/0057 606/213 |
| 2016/0081686 A1 * | 3/2016 | Miksza | A61B 17/0401 606/151 |

OTHER PUBLICATIONS

Office Action dated Aug. 15, 2012 in U.S. Appl. No. 12/654,978.
Notice of Allowance dated Jul. 27, 2015 in U.S. Appl. No. 13/35,587.
Office Action dated Mar. 16, 2016 in U.S. Appl. No. 14/947,598.
Notice of Allowance dated Jul. 5, 2016 in U.S. Appl. No. 14/947,598.
Notice of Allowance dated Oct. 30, 2016 in U.S. Appl. No. 15/338,419.

* cited by examiner

DEVICE AND PROCEDURE FOR PERICARDIAL PATCH TRANSCATHETER ATRIAL SEPTAL DEFECT CLOSURE

The present application is a Continuation Application of U.S. application Ser. No. 15/338,419, filed on Oct. 30, 2016, which is a Continuation-In-Part Application of U.S. application Ser. No. 14/947,598, filed on Nov. 20, 2015, now U.S. Pat. No. 9,480,469, which is a Continuation Application of U.S. application Ser. No. 13/835,587, filed on Mar. 15, 2013, now U.S. Pat. No. 9,192,365, which is a Divisional Application of U.S. application Ser. No. 12/654,978, filed on Jan. 12, 2010, now U.S. Pat. No. 8,398,658, which benefits a priority from U.S. Provisional Patent Application No. 61/154,388, filed on Feb. 21, 2009, the entire contents of which are incorporated herein by reference.

BACKGROUND OF THE INVENTION

Field of the Invention

The present invention relates to a method for providing a minimally invasive closure of atrial septal defect without cardiopulmonary bypass and, in particular, a device and a method for minimally invasive closure of atrial septal defect via a right minithoracotomy to deploy a pericardial patch under a transesophageal echocardiography guidance.

Description of the Related Art

There are currently two methods for the closure of atrial septal defect (ASD), conventional or minimally invasive surgical method and percutaneous device transcatheter closure. The former requires cardiopulmonary bypass (CPB), and the latter, which entails the deployment of a sizable device in the heart, is hampered by the defect size and circumferential margins adjacent to the superior and inferior venae cavae, pulmonary vein, mitral valve, and aortic sinus.

Recently, robotically assisted surgical systems have enhanced the precision of minimally invasive cardiac surgery. These costly procedures, however, still require the CPB. CPB is widely recognized as having a number of adverse effects, including generation of microemboli and an inflammatory response associated with increased cytokine production and complement activation, begetting neurological dysfunction in adults and neurodevelopmental dysfunction especially in children.

In addition, recently cosmetic sequelae following cardiac surgery has rendered minimal access approaches with equivalent results and a nearly invisible scar is more favorable.

SUMMARY OF THE INVENTION

In view of the foregoing and other exemplary problems, disadvantages, and drawbacks of the aforementioned devices and methods, it is an exemplary purpose of the present invention to provide a device and a method for minimally invasive closure of atrial septal defect without cardiopulmonary bypass.

The present invention includes a surgical device and method for closure atrial septal defect with minimally invasive approach. The device includes a head portion which is movable and includes a distal jaw placed distal relative to a person holding the surgical device, a guide rod which drives the distal jaw, and a plurality of first suture-guide channels attached to the distal jaw, and a body portion which is stationary and includes a cylindrical base, a proximal jaw attached to the cylindrical base, and a plurality of second suture-guide channels attached to the proximal jaw.

The guide rod drives the distal jaw to pass a pericardium patch through a patient's ASD while the proximal end remains extracorporeal. The first suture-guide channels and the second suture-guide channels guide a suture thread to suture the pericardium patch onto an ASD rim.

The head portion may include four first suture-guide channels, and the body portion may include four second suture-guide channels.

Further, each of the first suture-guide channels includes an arm which connects a center portion of each of the first suture-guide channels to the distal jaw. Each of the first suture-guide channels may be spaced apart from an adjacent one of the first suture-guide channels such that the arm of the each of the first suture-guide channels is oriented at 90 degrees with respect to an arm of the adjacent one of the first suture-guide channels.

Also, each of the second suture-guide channels includes an arm which connects a center portion of each of the second suture-guide channels to the proximal jaw. Each of the second suture-guide channels may be spaced apart from an adjacent one of the second suture-guide channels such that the arm of the each of the second suture-guide channels is oriented at 90 degrees with respect to an arm of the adjacent one of the second suture-guide channels. The first suture-guide channels may be oriented at 90 degrees to the second suture-guide channels such that the first suture-guide channels couple with the second suture-guide channels to form a circle.

In the surgical device, the first suture-guide channels are attached to a plurality of first arms, each of the first arms connects a center portion of each of the first suture-guide channels to the distal jaw. The first arms may be oriented at 0, 90, 180, and 270 degrees with respect to a center of the guide rod.

Further, the second suture-guide channels are attached to a plurality of second arms, each of the second arms connects a center portion of each of the second suture-guide channels to the proximal jaw. The second arms may be oriented at 45, 135, 225, and 315 degrees with respect to the center of the guide rod.

In the surgical device, the pericardial patch is connected to a suction device via a flexible pipe. Also, a threading thread attaches the pericardial patch to the distal jaw, in which ends of the threading thread are extracorporeal.

Further, a lever drives the distal jaw away from the proximal jaw such that the distal jaw and the proximal jaw are spaced on different sides of an ASD hole. After the suture thread sutures the pericardium patch, the lever pulls the distal jaw backward toward the proximal jaw such that the first suture-guide channels couple with the second suture-guide channels to form a circle.

The lever may include a wire and a spring or a crown wheel and a pinion. The level drives the distal jaw by pulling the wire.

In the surgical device, the first suture-guide channels and the second suture-guide channels guide a needle that carries the suture thread to suture the pericardium patch onto the ASD rim. The needle includes a long malleable needle, and passes the suture thread through a space between the guide rod and an internal section of the cylindrical base. The pericardium patch may be glued to the distal jaw.

Another aspect of the present invention includes a method of providing a surgical device for closure of atrial septal defect with minimally invasive approach.

The method includes drawing a pericardial patch over a distal jaw of the surgical device, while keeping a first suture-guide channels attached to the distal jaw and a second suture-guide channels attached to a proximal jaw of the surgical device closed, inserting the surgical device through a hole incised in an intercostal space of a patient and drawing the surgical device toward the ASD, while keeping the proximal end of the surgical device extracorporeal, manipulating forward a guide rod of the surgical device to drive the distal jaw to negotiate the distal jaw through the ASD, opening the first suture-guide channels and the second suture-guide channels to position the first suture-guide channels and the second suture-guide channels around the ASD, withdrawing the distal jaw such that the distal jaw latches onto the proximal jaw, pulling back the pericardial patch in conjunction with an ASD rim to secure the pericardial patch and the ASD rim between the first suture-guide channels and the second suture-guide channels, employing a long malleable needle extracorporeally to pass a suture thread into a space between the guide rod and an internal part of a cylindrical base, which supports a body portion of the surgical device, to suture the pericardial patch onto the ASD rim through the first suture-guide channels and the second suture-guide channels, re-steering forward the distal jaw to release the pericardial patch and to suture the pericardial patch onto the ASD rim, shutting the first suture-guide channels and the second suture-guide channels into respective original positions on the distal jaw and the proximal jaw, withdrawing the distal jaw from the ASD and lodging the distal jaw upon the proximal jaw, removing the surgical device from a body of the patient, and orienting a plurality of knots extracorporeally toward the ASD to complement the suture of the pericardial patch.

The first suture-guide channels may be attached to a plurality of first arms, each of the first arms connects a center portion of each of the first suture-guide channels to the distal jaw. The first arms may be oriented at 0, 90, 180, and 270 degrees with respect to a center of the guide rod. The second suture-guide channels may be attached to a plurality of second arms. Each of the second arms connects a center portion of each of the second suture-guide channels to the proximal jaw. The second arms may be oriented at 45, 135, 225, and 315 degrees with respect to the center of the guide rod.

In the method, after the suture thread sutures the pericardium patch, a lever pulls the distal jaw backward toward the proximal jaw such that the first suture-guide channels couple with the second suture-guide channels to form a circle.

Further, each of the first suture-guide channels includes an arm which connects a center portion of each of the first suture-guide channels to the distal jaw. Each of the first suture-guide channels is spaced apart from an adjacent one of the first suture-guide channels such that the arm of the each of the first suture-guide channels may be oriented at 90 degrees with respect to an arm of the adjacent one of the first suture-guide channels. Each of the second suture-guide channels comprises an arm which connects a center portion of each of the second suture-guide channels to the proximal jaw.

Each of the second suture-guide channels is spaced apart from an adjacent one of the second suture-guide channels such that the arm of the each of the second suture-guide channels may be oriented at 90 degrees with respect to an arm of the adjacent one of the second suture-guide channels. The first suture-guide channels may be oriented at 90 degrees to the second suture-guide channels such that the first suture-guide channels couple with the second suture-guide channels to form a circle.

With its unique and novel features, the present invention provides a device and a method for minimally invasive approach for the closure of all forms and sizes of secundum ASD which obviates the need for CPB, radiation, and deployment of an expensive bulky device in the heart. This procedure is carried out via a right minithoracotomy to deploy a pericardial patch under transesophageal echocardiography guidance. The method of the present invention does not require additional work for the closure of more than one defect with aneurismal rims or defects with deficient margins. Further, it offers an added element of safety compared with the transcutaneous route, because the procedure is performed in an operating room with CPB facilities available for any exigencies. This approach also minimizes the risk of atrioventricular valve distortion and obstruction of the superior and inferior venae cavae or coronary sinus.

Other advantages of this technique are reduced associated pain, better cosmetic results, shorter recovery time, and fewer complications.

BRIEF DESCRIPTION OF THE DRAWINGS

The foregoing and other exemplary purposes, aspects and advantages will be better understood from the following detailed description of the exemplary embodiments of the invention with reference to the drawings, in which.

DETAILED DESCRIPTION OF THE EXEMPLARY EMBODIMENTS OF THE INVENTION

Figure 1:
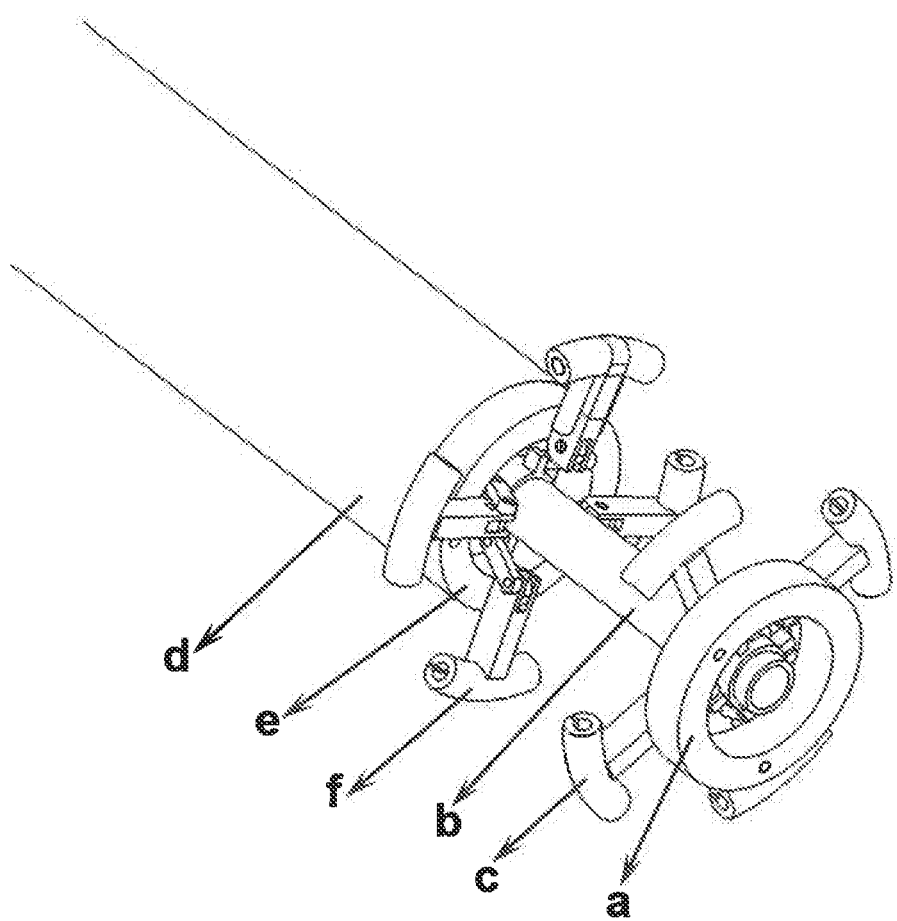
FIG. 1 illustrates an exemplary device for minimally invasive closure of atrial septal defect, in accordance with an exemplary aspect of the present invention.

Referring now to the drawings, FIG. 1 illustrates an exemplary aspect of the present invention. Specifically, FIG. 1 illustrates an exemplary device 100 for minimally invasive closure of atrial septal defect without cardiopulmonary bypass, in accordance with an exemplary aspect of the present invention.

As shown in FIG. 1, the device includes two main parts, a head, which is moveable and includes of a guide rod (b), distal jaw, relative to the person holding the device (a), and 4 suture-guide channels (c), and a body, which is stationary and includes a cylindrical base (d), a proximal jaw (e), relative to the person who holds the device, and 4 suture-guide channels (t). The 8 suture-guide channels (c) and (f), oriented at 90 degrees relative to one another and mounted upon the distal jaw (a) and proximal jaw (e), form a circle, with the channels at the distal jaw (a) being at 0, 90, 180, and 270 degrees and the channels at the proximal jaw (e) being at 45, 135, 225, and 315 degrees such that the channels can slide open and shut radially.

A 3-cm incision is arranged in the right fourth midaxillary intercostal space. The lateral mini thoracotomy exposes the pericardium, which is opened and sutured with five 2-0 stay sutures to suspend the heart. Right atriotomy follows the placement of two parallel 4-0 polypropylene purse string sutures, approximately 10 mm in diameter. The patient is then administered about 1.0 mg/kg of heparin, and the activated clotting time is confirmed to be greater than 250 s.

Figure 2A:
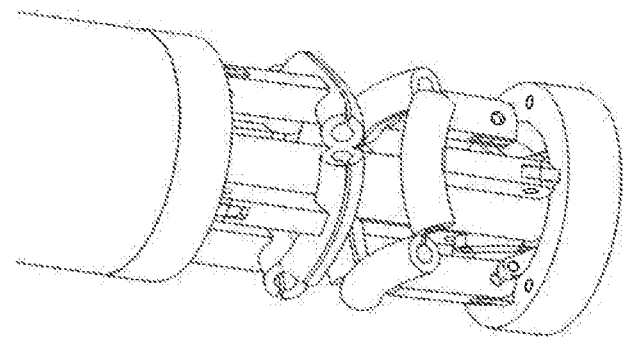
FIG. 2a illustrates a view of the distal jaw while the suture-guide channels remain shut, before drawing a pericardium patch over the device for minimally invasive closure of atrial septal defect, in accordance with an exemplary aspect of the present invention.
Figure 2B:
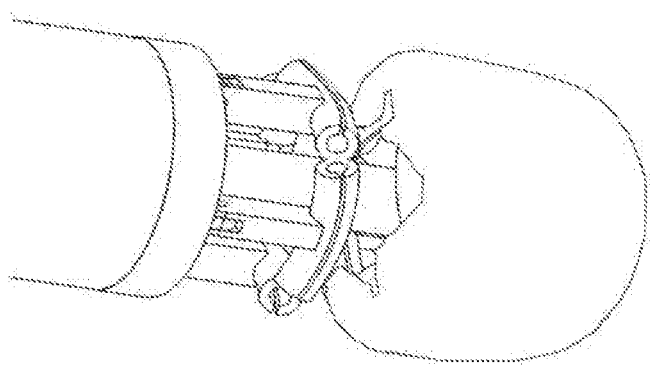
FIG. 2b illustrates a view of the distal jaw while the suture-guide channels remain shut, after drawing a pericardium patch over the device for minimally invasive closure of atrial septal defect, in accordance with an exemplary aspect of the present invention.

A pericardium patch, with the desired size for the closure of ASD, is cut and drawn over the distal jaw (a) while the suture-guide channels (c) and (f) remain shut, as shown in the exemplary FIGS. 2a and 2b.

Figure 3:
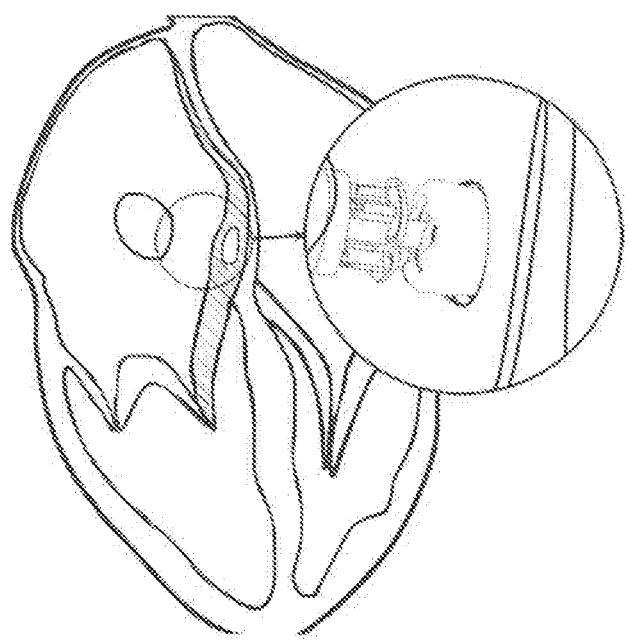
FIG. 3 illustrates a cross section view of heart, the ASD, and the distal jaw of the device while it advanced toward the ASD, in accordance with an exemplary aspect of the present invention.

The device is thereafter inserted through the hole incised in the patient's intercostal space and advanced toward the ASD, while the proximal end of the device body, relative to the person using the device, remains extracorporeal, as illustrated in the exemplary FIG. 3.

The guide rod (b) is manipulated to drive the distal jaw (a) forward and negotiate it through the ASD.

Figure 4:
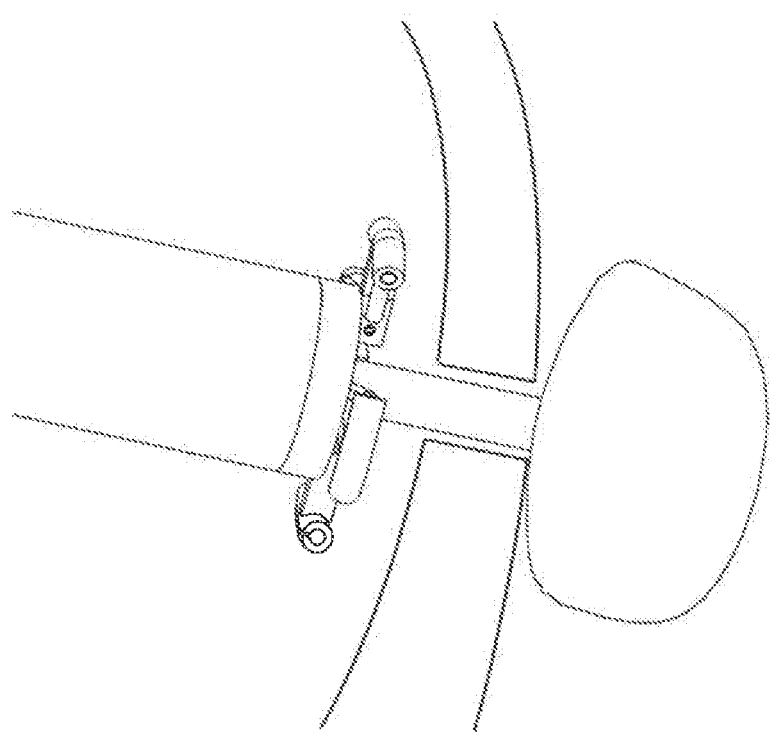
FIG. 4 illustrates a cross sectional view of the ASD while the suture-guide channels are opened and positioned around, in accordance with an exemplary aspect of the present invention.

As shown in the exemplary FIG. 4, in this exemplary aspect, the suture-guide channels (c) and (f) are subsequently opened and positioned around the ASD.

Figure 5A:
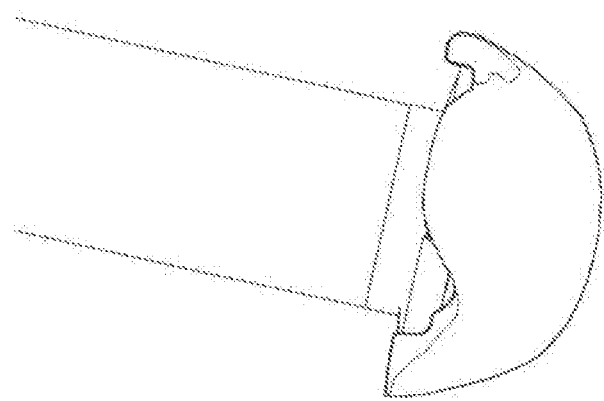
FIG. 5a illustrates a view of the device when the distal jaw is withdrawn and pericardium patch in conjunction with the ASD rim is firmly secured between the suture-guide channels, in accordance with an exemplary aspect of the present invention.
Figure 5B:
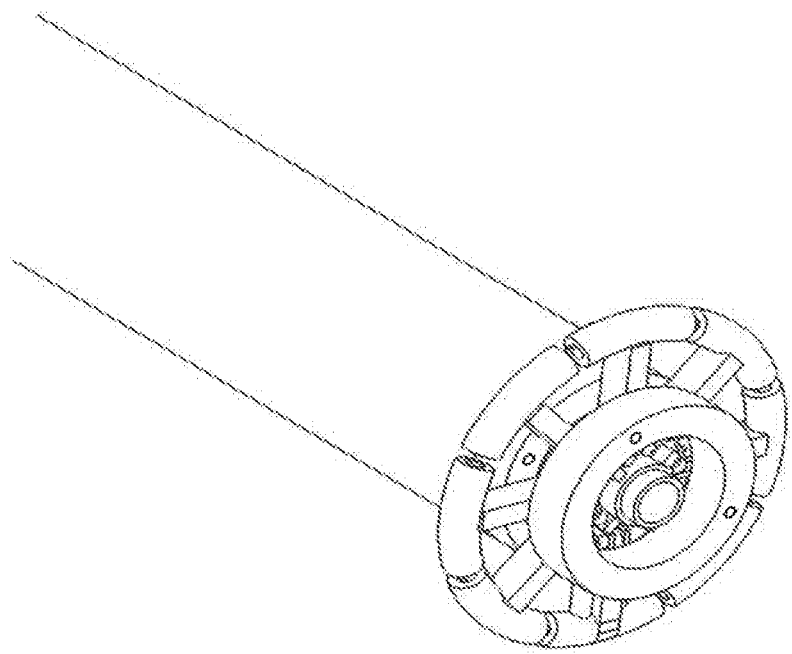
FIG. 5b illustrates a view of the device when the distal jaw is withdrawn and latches onto the proximal jaw, in accordance with an exemplary aspect of the present invention.

The distal jaw (a) is withdrawn so that it latches onto the proximal jaw (e), to pull back the pericardium patch in conjunction with the ASD rim and firmly secure them between the suture-guide channels (c) and (f), as depicted in the exemplary FIGS. 5a and 5b.

A long malleable needle is employed extracorporeally to pass a suture thread into the space between the guide rod (b) and the internal part of the cylindrical base (d) and to suture the pericardium patch onto the ASD rim through the suture-guide channels (c) and (f).

Figure 6:
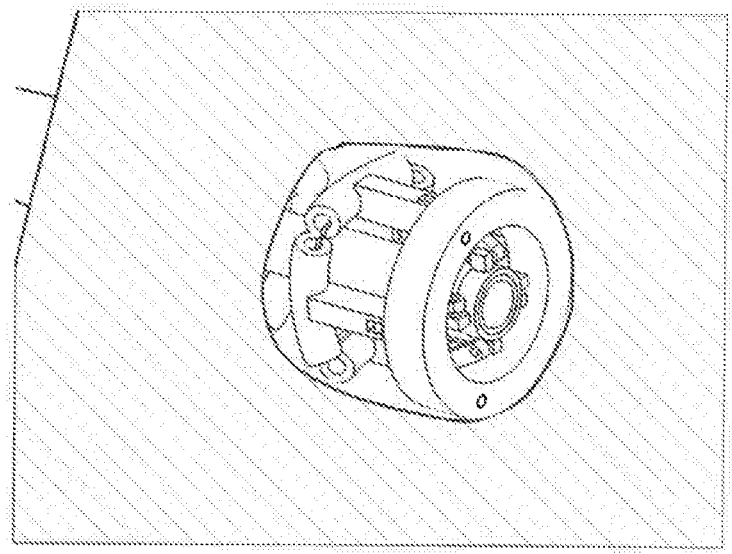
FIG. 6 illustrates a view of the device while the distal jaw is re-steered forward to releases the pericardium patch for snugly suturing onto the ASD rim, in accordance with an exemplary aspect of the present invention.

The distal jaw (a) is re-steered forward so that it releases the pericardium patch, which is snugly sutured onto the ASD rim, as illustrated in the exemplary FIG. 6.

Figure 7:
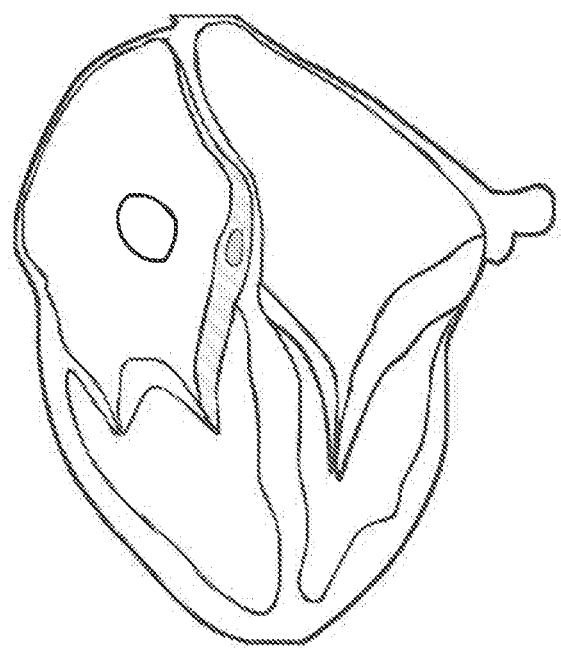
FIG. 7 illustrates cross section view of the heart after closure of the ASD, in accordance with an exemplary aspect of the present invention.

The suture-guide channels (c) and (f) are shut and retracted to their respective original positions on the jaws. The distal jaw (a) is afterward withdrawn through the ASD and is lodged upon the proximal jaw (e), as shown in the exemplary FIG. 7.

Then, the device is extracted from the patient's body. Finally, a desired number of knots are arranged extracorporeally and the knots are then oriented toward the ASD so as to complement the suturing of the pericardium patch. The chest is closed as per normal with no drainage tube placement.

Another exemplary aspect of the present invention is directed to a method of providing a surgical device for closure of ASD with minimally invasive approach.

The method includes drawing a pericardial patch over a distal jaw of the surgical device, while keeping a first suture-guide channels attached to said distal jaw and a second suture-guide channels attached to a proximal jaw of the surgical device closed, inserting the surgical device through a hole incised in an intercostal space of a patient and drawing the surgical device toward the ASD, while keeping the proximal jaw of the surgical device extracorporeal, manipulating forward a guide rod of the surgical device to drive the distal jaw to negotiate the distal jaw through the ASD, opening the first suture-guide channels and the second suture-guide channels to position the first suture-guide channels and the second suture-guide channels around the ASD, withdrawing the distal jaw such that the distal jaw latches onto the proximal jaw, pulling back the pericardial patch in conjunction with an ASD rim to secure the pericardial patch and the ASD rim between the first suture-guide channels and the second suture-guide channels, employing a malleable needle extracorporeally to pass a suture thread into a space between the guide rod and an internal part of a cylindrical base, which supports a body portion of the surgical device, to suture the pericardial patch onto the ASD rim through the first suture-guide channels and the second suture-guide channels, re-steering forward the distal jaw to release the pericardial patch and to suture the pericardial patch onto the ASD rim, shutting the first suture-guide channels and the second suture-guide channels into respective original positions on the distal jaw and the proximal jaw, withdrawing the distal jaw from the ASD and lodging the distal jaw upon the proximal jaw, removing the surgical device from a body of the patient, and orienting a plurality of knots extracorporeally toward the ASD to complement said suture of the pericardial patch.

The method may further include driving the distal jaw away from the proximal jaw by a lever such that the distal jaw and the proximal jaw are spaced on different sides of an ASD hole, and after the suture thread sutures the pericardium patch, pulling the distal jaw backward toward the proximal jaw by the lever such that the first suture-guide channels couple with the second suture-guide channels to form a circle.

Figure 8:
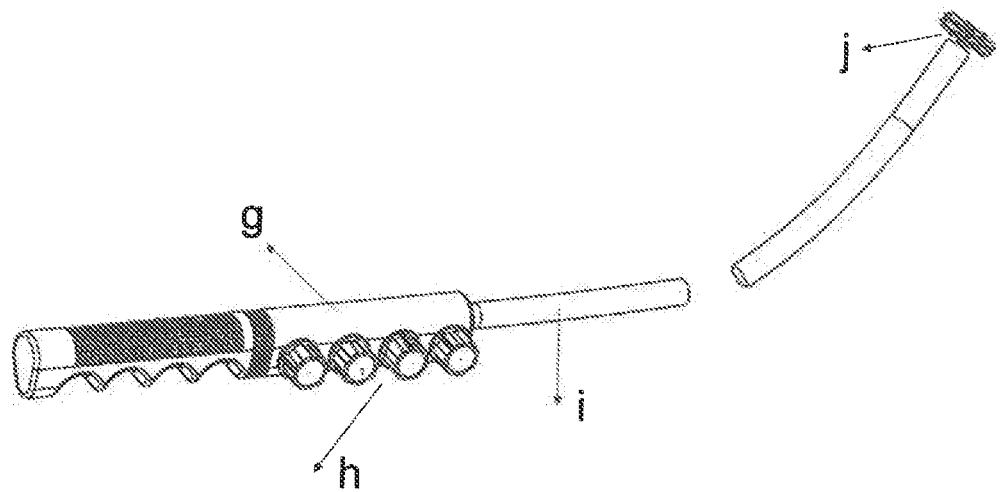
FIG. 8 illustrates an exemplary device for transcatheteral closure of atrial septal defect, in accordance with an exemplary aspect of the present invention.

FIG. 8 illustrates an exemplary aspect of the second device of the present invention. Specifically, FIG. 8 illustrates an exemplary device for transcathetral closure of atrial septal defect without cardiopulmonary bypass, in accordance with an exemplary aspect of the present invention.

Figure 9:
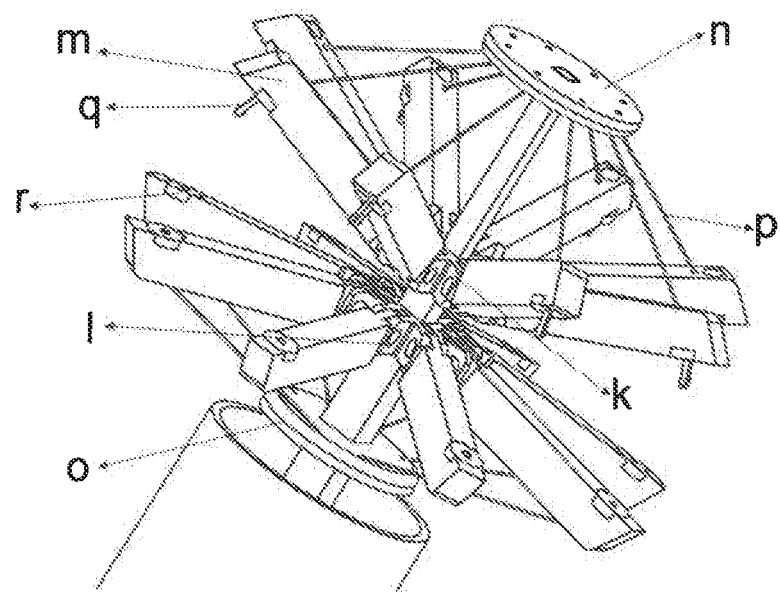
FIG. 9 illustrates the head portion of device for transcatheteral closure of atrial septal defect, in accordance with an exemplary aspect of the present invention.

As shown in FIG. 8, the device consists of two parts: a guide (g) and a head (j). The guide is comprised of guide knobs (h), which move the guide levers forward and backward via a rod (i) and control the different components of the head (j). The head itself comprises various parts, depicted in FIG. 9. The head has two main parts: the distal jaw (k) (the jaw which is distal relative to the operator) and the proximal jaw (l). Each jaw has 8 arms (m), which close through the pull of the strings (p) when the distal disc (n) moves forward and the proximal disc (o) moves backward or vice versa open through the direct pressure on the arms (m) when the distal disc (n) moves backward and the proximal disc (o) moves forward. When the arms (m) on both jaws (k & l) are completely open, the pins (q) and the sockets (r) are aligned. The pins (q) and the sockets (r) can be completely engaged with the simultaneous forward pressure of the entire proximal jaw (l) and the backward pressure of the entire distal jaw (k). When the distal jaw (k) moves forward and the proximal jaw (l) moves backwards simultaneously, the pins (q) and the sockets (r) are released.

Figure 10A:
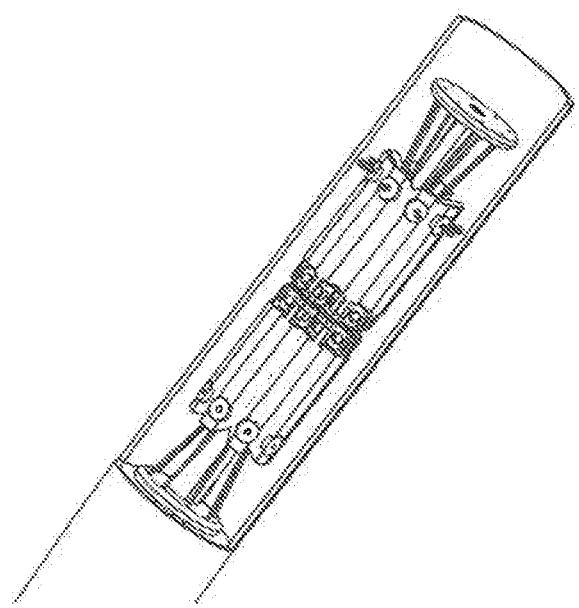
FIG. 10a illustrates a view of the head while the arms of both distal and proximal jaws remain shut, before drawing a pericardium patch over the device for transcatheteral closure of atrial septal defect, in accordance with an exemplary aspect of the present invention.
Figure 10B:
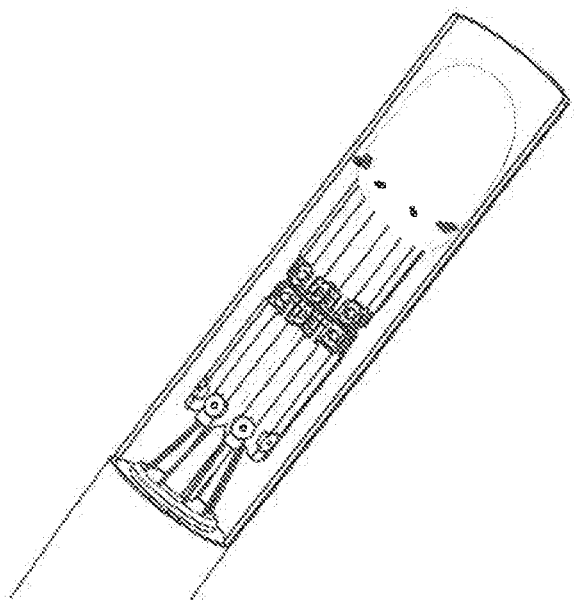
FIG. 10b illustrates a view of the head while the arms of both distal and proximal jaws remain shut, after drawing a pericardium patch over the device for transcatheteral closure of atrial septal defect, in accordance with an exemplary aspect of the present invention.
Figure 11:
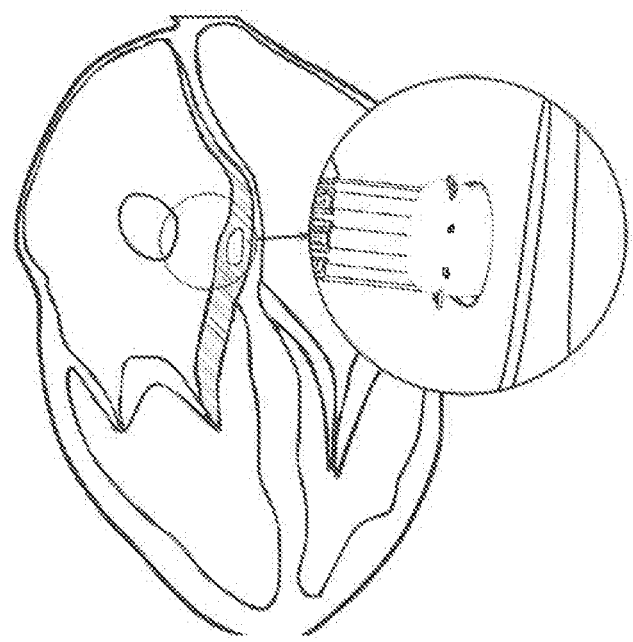
FIG. 11 illustrates a cross section view of heart, the ASD, and the distal jaw of the device while it advanced toward the ASD, in accordance with an exemplary aspect of the present invention.
Figure 12:
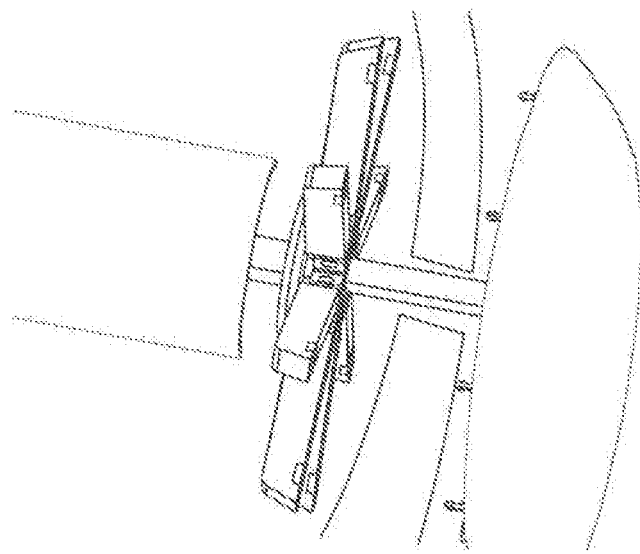
FIG. 12 illustrates a cross sectional view of the ASD while the both jaws are opened and positioned around, in accordance with an exemplary aspect of the present invention.
Figure 13:
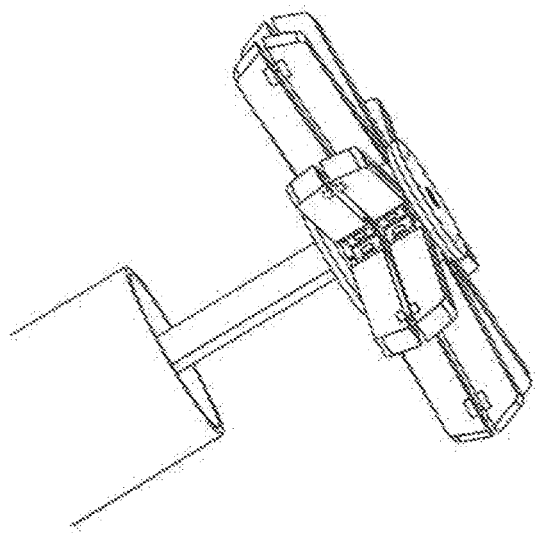
FIG. 13 illustrates a view of the device when the distal jaw is withdrawn and pericardium patch in conjunction with the ASD rim is firmly secured between distal and proximal jaws and pins lached into the sockets, in accordance with an exemplary aspect of the present invention.
Figure 14:
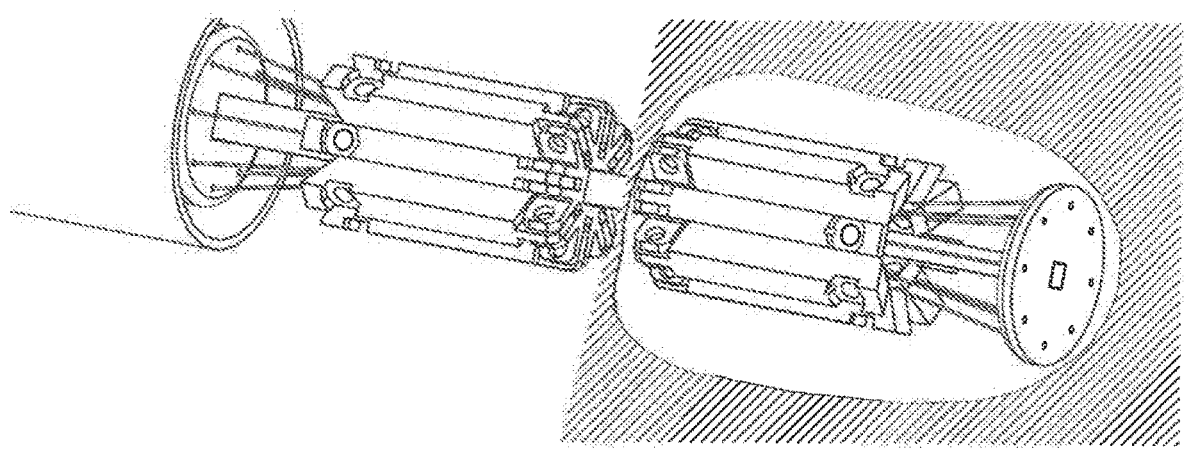
FIG. 14 illustrates a view of the device while the distal jaw is re-steered forward to releases the pericardium patch for snugly fixing onto the ASD rim, in accordance with an exemplary aspect of the present invention.

A pericardium patch, with the desired size for the closure of the ASD, is cut and drawn over the distal jaw (k) while the arms (m) remain shut and both jaws (k & l) are in the rod (i) (FIG. 10*a* and FIG. 10*b*). The rod (i) is entered into the jugular or femoral vein and is moved to the proximity of the ASD. Thereafter, the distal jaw (k) is steered forward by tweaking the guide knobs (h) while the proximal jaw (l) of the device remains extracorporeal (FIG. 11). The arms (m) on both jaws (k & l) are subsequently opened by moving the distal disc (n) and the proximal disc (o) with a tweak of the guide knobs (h) and are positioned around the ASD (FIG. 12). Next, the distal jaw (k) is withdrawn so that it latches onto the proximal jaw (l), pulling back the pericardium patch in conjunction with the ASD rim and firmly securing them between the arms (m). The pins (q) latch into the sockets (r) and secure the pericardium around the ASD (FIG. 13). The distal jaw (k) and the proximal jaw (l) are re-steered forward and backward so that they can release the pins (q), the sockets (r), and the pericardium patch—with the latter eventually becoming snugly fixed onto the ASD rim (FIG. 14). The distal jaw (k) is afterward withdrawn through the ASD and is lodged upon the proximal jaw (l). The head (j) is withdrawn into the rod (i) and extracted from the patient's body. The pins (q) and the sockets (r) are made of material compatible with the body and after a while, the empty space between them and they themselves will be covered with the proper tissue.

The device and method of the present invention enables that the minimally invasive closure of atrial septal defect procedure be performed in the operating room with CPB facilities available for any exigencies. This approach also minimizes the risk of atrioventricular valve distortion and obstruction of the superior and inferior venae cavae or coronary sinus.

While the invention has been described in terms of one or more embodiments, those skilled in the art will recognize that the invention can be practiced with modification within the spirit and scope of the appended claims. Specifically, one of ordinary skill in the art will understand that the drawings herein are meant to be illustrative, and the design of the inventive assembly is not limited to that disclosed herein but may be modified within the spirit and scope of the present invention.

Further, Applicants' intent is to encompass the equivalents of all claim elements, and no amendment to any claim the present application should be construed as a disclaimer of any interest in or right to an equivalent of any element or feature of the amended claim.

What is claimed is:

1. A device for closure of an atrial septal defect (ASD) by deploying a pericardial patch, said device comprising:
   a head comprising a distal jaw and a proximal jaw; and
   a distal disc attached to the distal jaw and a proximal disc attached to the proximal jaw,
   wherein each of the distal jaw and the proximal jaw includes at least one arm which closes when the distal disc moves forward and the proximal disc moves backward,
   wherein, based on an engagement status of a distal engagement portion, located on the at least one arm of the distal jaw, with a proximal engagement portion located on the at least one arm of the proximal jaw, the pericardial patch deploys to close the ASD, and
   wherein, when the at least one arm of the distal jaw and the at least one arm of the proximal jaw are completely open, the distal engagement portion and the proximal engagement portion engage with each other.

2. The device of claim 1, wherein the distal engagement portion comprises a pin and the proximal engagement portion comprises a socket.

3. The device of claim 2, wherein, when the at least one arm of the distal jaw and the at least one arm of the proximal jaw are completely open, the pin and the socket engage with each other.

4. The device of claim 3, wherein, when the distal jaw moves forward and the proximal jaw moves backwards, the pin disengage from the socket.

5. The device of claim 1, further comprising a guide that comprises guide knobs which move guide levers of the guide forward and backward via a rod to control the head.

6. The device of claim 1, wherein, when the distal disc moves forward and the proximal disc moves backward, the at least one arm of the distal jaw and the at least one arm of the proximal jaw close.

7. The device of claim 6, wherein, when the distal disc moves backward and the proximal disc moves forward, the at least one arm of the distal jaw and the at least one arm of the proximal jaw open.

8. The device of claim 1, wherein, when the distal jaw moves forward and the proximal jaw moves backwards, the distal engagement portion disengages from the proximal engagement portion.

9. The device of claim 1, wherein, when the at least one arm of the distal jaw and the at least one arm of the proximal jaw are completely open, the distal engagement portion and the proximal engagement portion engage with each other with a forward pressure of the proximal jaw and a backward pressure of the distal jaw.

10. The device of claim 9, wherein, when the distal jaw moves forward and the proximal jaw moves backwards, the distal engagement portion disengages from the proximal engagement portion.

11. The device of claim 1, wherein the pericardium patch is configured to drawn over the distal jaw while the at least one arm of the distal jaw and the at least one arm of the proximal jaw are in a rod.

12. The device of claim 1, further comprising a guide that comprises guide knobs,
   wherein, when the guide knobs are actuated, the at least one arm of the distal jaw and the at least one arm of the proximal jaw open by moving the distal disc and the proximal disc to deploy the pericardial patch configured to close the ASD.

13. The device of claim 1, further comprising:
   strings connecting the at least one arm of the distal jaw to the distal disc and further connecting the at least one arm of the proximal jaw to the proximal jaw.

14. The device of claim 13, wherein, when the distal disc moves forward and the proximal disc moves backward, the distal jaw pulls the strings to close the at least one arm of the distal jaw, and the proximal disc pulls the strings to close the at least one arm of the proximal jaw.

15. The device of claim 14, wherein, when the distal disc moves backward and the proximal disc moves forward, the distal jaw releases the strings to open the at least one arm of the distal jaw, and the proximal disc releases the strings to open the at least one arm of the proximal jaw.

\* \* \* \* \*